United States Patent
Martin et al.

(10) Patent No.: US 7,845,292 B2
(45) Date of Patent: Dec. 7, 2010

(54) PROCESS FOR SLAG AND CORROSION CONTROL IN BOILERS

(75) Inventors: J. David Martin, Elburn, IL (US); Christopher R. Smyrniotis, St. Charles, IL (US); Kent W. Schulz, Geneva, IL (US); William H. Sun, Lisle, IL (US); Scott K. Bohlen, Bucksport, ME (US); Glenn Brewer, Newmarket, NH (US)

(73) Assignee: Fuel Tech, Inc., Warrenville, IL (US)

( * ) Notice: Subject to any disclaimer, the term of this patent is extended or adjusted under 35 U.S.C. 154(b) by 539 days.

(21) Appl. No.: 11/548,866

(22) Filed: Oct. 12, 2006

(65) Prior Publication Data

US 2007/0119352 A1    May 31, 2007

Related U.S. Application Data

(63) Continuation-in-part of application No. 11/383,646, filed on May 16, 2006.

(60) Provisional application No. 60/681,786, filed on May 17, 2005.

(51) Int. Cl.
    *F23B 90/00*    (2006.01)
    *C10L 10/04*    (2006.01)

(52) U.S. Cl. .................. 110/343; 431/3; 432/2

(58) Field of Classification Search .......... 110/343, 110/347; 431/3, 2; 432/2
    See application file for complete search history.

(56) References Cited

U.S. PATENT DOCUMENTS

| | | | | |
|---|---|---|---|---|
| 3,259,461 | A * | 7/1966 | Griffin, Jr. et al. | 436/6 |
| 3,861,876 | A * | 1/1975 | Robertson et al. | 436/6 |
| 3,864,458 | A * | 2/1975 | Roberts | 423/481 |
| 5,353,722 | A * | 10/1994 | Vassiliou et al. | 110/346 |
| 5,894,806 | A * | 4/1999 | Smyrniotis et al. | 110/343 |
| 6,478,948 | B2 * | 11/2002 | Breen et al. | 205/740 |
| 6,677,765 | B2 * | 1/2004 | Breen et al. | 324/691 |
| 6,997,119 | B2 * | 2/2006 | Radway | 110/343 |

* cited by examiner

*Primary Examiner*—Kenneth B Rinehart
*Assistant Examiner*—David J Laux
(74) *Attorney, Agent, or Firm*—Thaddius J. Carvis (57) ABSTRACT

A slag and corrosion control process is described. The process entails: identifying the location of at least one slagging problem area in a boiler; introducing a slag control chemical comprising magnesium oxide or hydroxide into combustion gases in a location identified as having a slagging problem; identifying the location of at least one corrosion problem area in a boiler; and introducing a corrosion control chemical comprising a sulfate salt, bisulfite salt, sulfuric acid, or sulfur into combustion gases in a location identified as having a corrosion problem. In operation, these slag deposits will be sufficiently friable to be removed by relatively moderate application of physical energy, thus saving time and reducing any damage to the tubes by the cleaning process. The slag deposits are less voluminous and less in weight and are removed quickly. It is an advantage of the invention that slag can be removed with little or no shut down of a boiler.

11 Claims, 2 Drawing Sheets

PROCESS FOR SLAG AND CORROSION CONTROL IN BOILERS

RELATED APPLICATION AND PRIORITY CLAIM

This application is a continuation-in-part of prior U.S. patent application Ser. No. 11/383,646, filed May 16, 2006, which is related to and claims priority to prior U.S. Provisional Patent Application No. 60/681,786 filed May 17, 2005, the disclosures of both of which are incorporated herein by reference in their entireties.

BACKGROUND OF THE INVENTION

The invention relates to a slag and corrosion control process, which is especially useful in the control of both slag and chloride corrosion in boilers, particularly waste to energy (WTE) and biomass boilers. Super heater tubes in WTE boilers are particularly susceptible to slagging and corrosion. Economical solutions to these problems are essential if this technology is to reach its fullest potential to the environment and national and enterprise energy security.

In the United States, WTE boilers have been built and operated primarily for environmental reasons. It would be desirable to improve their economics so that economic incentives would be added to environmental concerns.

WTE boilers burn solid waste, e.g., refuse derived fuels (RDF) made from solid municipal waste, and eliminate the need for large tracts of land to be set aside for solid waste disposal. They partially offset capital and operating costs by generating electrical power and/or steam energy. It would be desirable from the standpoint of the environment and energy security to foster their wider use. Because economics will always play a significant role in the choice between WTE plants and landfills, it is important to find ways to reduce costs for WTE plants.

The generation of solid waste follows population density, which places economic pressure on landfill availability and costs. The economics of WTE plants is a complex matter. As it stands today, WTE installations are economically competitive with landfills in more populated areas but have not seen widespread use in areas where land is still plentiful. The selection of a WTE plant instead of landfill is dependent on many cost factors including the cost of landfill operations, the cost of transporting waste to the landfill, the cost of generating electricity by burning fossil fuels, the cost of WTE plant installation, the cost of WTE operation, and many other costs including those for maintenance and repair of the WTE plants. Where the maintenance costs can be decreased, the installation and use of WTE plants and their positive benefit to the environment will be increased because improved economics will foster their wider usage.

The current operational and maintenance costs associated with slagging and, especially, corrosion in WTE boilers create economic burdens now, but their efficient control offers significant savings. The problem of corrosion in WTE plants is so severe that it has deterred their more widespread adoption for economic reasons. Better heat recovery could be achieved by reducing slagging, and boilers could be run more regularly if slagging could be reduced and/or made easier to remove. Both better heat recovery and more regular operation will improve the economics of WTE plants versus power plants burning fossil fuels. Improving economics will provide an eventual increase in the use of WTE and will also provide benefits in energy security because fossil fuels will be replaced to at least some significant degree by using RDF, which is projected to remain available in vast quantities.

Because the problems of slagging and corrosion are so large for WTE boilers, solution of these problems offer great incentives for more widespread use of this technology. The RDF as typically burned tends to be highly corrosive and to promote slagging. Because plastics and other materials of commerce that find their way into municipal solid waste can contain more halogens, e.g., chlorides, than typical fossil fuels, the problem of corrosion for WTE facilities has grown in importance as these plants take on greater environmental and economic importance. Slagging reduces heat transfer from the combustion gases to water held in heat exchangers, and removing slag from heat exchange surfaces is costly. Slag removal adds two-fold costs: it typically requires shutting the facility down for cleaning, and the materials and manpower required for cleaning add further costs. There is a need to address both corrosion and slag control with new technology that can increase the overall economics of WTE boilers and foster their use for improving the environment and contributing to national energy security.

Slagging deposits are sometimes extremely difficult to remove by conventional techniques such as soot blowing. Slag buildup results in a loss of heat transfer throughout the system, increases draft loss, limits gas throughput and is a factor in tube failure due to erosion from excessive soot blowing. A variety of procedures are known for adding treatment chemicals to the fuel or into the furnace in quantities sufficient to treat all of the ash produced, in the hope of solving the slagging problem. More recent technology provides for targeted chemical introduction where the chemical is directed at trouble spots in a boiler. Typical slag control chemicals include magnesium oxide and magnesium hydroxide. See, in this regard, U.S. Pat. Nos. 5,740,745 and 5,894,806 and U.S. Patent Publication No. 20050150441 and the references cited therein. While these chemicals can reduce the severity of slagging and make cleaning significantly easier, they have not been developed to the extent desired to fully achieve the economic and environmental advantages of WTE facilities. It would be desirable, for example, to so reduce the severity of slagging that the reduced application of mechanical energy could effectively clean heat exchange surfaces with little or no boiler shut down. It would also be desirable if the slag that did form could be removed without excessive tube erosion, which can be caused by chemical reactions with iron in the tubes as well as the mechanical efforts to remove tough slag deposits.

Over several recent years the literature has extensively reported that chloride induced corrosion of high temperature surfaces in waste to energy boilers is one of the most costly problems in the industry. This problem can result in replacement of superheater pendants as often as every eight months in some units or the costly use of higher alloyed materials to either shield the metal surfaces or serve as replacement tube material.

The cost-effectiveness of the replacement alloys has not been proven in many cases, and the industry has been looking for alternative solutions. There is a need for chemical solutions to the problem of corrosion in boilers of all types and especially in the high temperature flue gas near WTE superheater pendants.

The problem of corrosion is not limited to WTE boilers. In U.S. Pat. No. 6,478,948, Breen, et al., indicate that until recently, furnace boiler tubes corroded slowly and had a service life of 20 to 30 years, but the introduction of low $NO_x$ burners has increased the rate of boiler tube corrosion and can reduce their life expectancy to only 1 to 2 years. Breen, et al., point out that the corrosion of furnace wall tubes involves several mechanisms. First, they say that removal of oxide film from the tubes eliminates protection from the oxide layer and allows further oxidation. Second, they say that if the oxide film is not present, the iron surface is attacked and pitted by condensed phase chlorides which may be present. They also point to a third mechanism which occurs when wet slag runs across the surface of the film. As that happens, iron from the tube goes into the slag solution which contains low fusion calcium-iron-silicate eutectics that are formed in the liquid slag under reducing conditions in the furnace. They state that reduced sulfur in the form of S, $H_2S$, FeS or $FeS_2$ can react with the oxygen of the tube scale depriving the tube metal of its protective layer.

Corrosion can be especially severe in WTE boilers, with areas operating at temperatures within the range of from about 250° C. to about 550° C., such as super heater pendant tubes, can particularly troublesome and costly. While the problems of boiler corrosion are well documented and there is a growing understanding of the causes, the available solutions to these problems are not as easily facilitated or economical as would be desired. In a 2004 paper delivered at NAWTEC, Ken Robbins of Maine Recovery Company detailed attempts to use shielding, alternate metallurgies, and various soot blowing strategies to mitigate corrosion found in a WTE unit. The paper also discussed a proprietary chemical slag control program, which was found helpful in controlling slag and minimizing cleaning outages, but had no discernable effect on specific localized corrosion problems. In the case of isolated corrosion, especially on superheater pendant surfaces, which can experience corrosion rates ranging from 0.020 to 0.050 inches per month, tube failures can occur in as little as seven months and create a need for replacement of the entire pendant annually.

A TNO (Nederlandse Organisatie Toegepast-Voor Natur-wetenschappelijk) report entitled "Review on Corrosion in Waste Incinerators and Possible Effect of Bromine" provides a mechanistic explanation for the severe corrosion suffered by WTE units. See Ir. P. Rademakers (TNO IND), Ing. W. Hesseling (TNO-MEP), Ir. J. van de Wetering (Akzo Nobel AMC) (July 2002). In addition to the overall analysis of the primary chemical components involved in this corrosion mechanism, it provides a series of equations that may explain why chloride corrosion occurs at the temperature and metallurgical conditions of a waste incinerator.

It is well known that corrosion by high CO levels and reducing atmospheres occurs in the first pass above the grate in-furnace. A refractory lining is often employed on the water walls in the first pass. A strong temperature gradient and condensing substances can also contribute to reducing conditions in these areas. Alkali metal chlorides have been found in deposits near the metal surface, and the high level of chlorides in the waste are strongly implicated with the problem.

Rademakers, et al., explain that high temperature corrosion in waste incinerators is caused by chlorine either in the form of HCl, $Cl_2$, or combined with Na, K, Zn, Pb, Sn and other elements. Both gaseous HCl with and without a reducing atmosphere and molten chlorides within the deposit, are considered major factors. As with Breen, et al, they point out that sulfur compounds can be corrosive compounds under some circumstances and can influence the corrosion by chlorine.

Rademakers, et al., identify several factors as the most important in high temperature corrosion: the metal temperature and the temperature difference between gas and metal, the flue gas composition, deposits formation and reducing conditions, and the ratio of $SO_2/HCl$. They indicate that following mechanisms can be distinguished:

Corrosion by $HCl/Cl_2$ or $SO_2/SO_3$ containing gas under oxidizing or oxidizing/reducing conditions, and Corrosion by solid or molten deposits of metal chlorides and sulfates.

Figure 1:
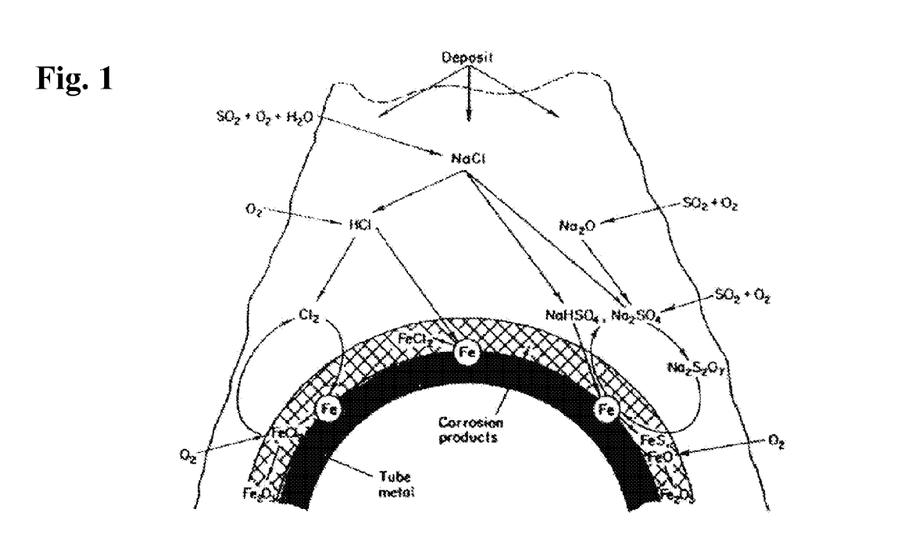
FIG. 1 is a schematic outlining the various steps of chemical reactions to help explain corrosion of incinerator boiler tubes.

Rademakers, et al., describe these mechanisms and refer to a schematic, in FIG. 1, as drawn from Krause, 1986, 1993, and as set out below in various steps.

Corrosion caused by chlorine-containing gas at metal temperatures above about 450° C. is referred to as 'active oxidation'. Alkali chlorides, such as NaCl, $CaCl_2$ and KCl, can be present already or can be formed by the combustion and subsequent reaction of alkali oxides:

$$Na_2O+2HCl=2NaCl+H_2O \qquad [1]$$

Under ideal conditions (good mixing, sufficient residence time) alkali chlorides can be sulfated according to the following reaction, provided there is enough $SO_2$ and $O_2$:

$$2NaCl+SO_2+\tfrac{1}{2}O_2+H_2O=Na_2SO_4+2HCl \qquad [2]$$

This would result in formation of sulfates and volatile HCl. At the relatively low tube wall temperatures of most waste incinerators, the sulfates are not very harmful and the HCl formed will be transported to the flue gas clean up system. However, if the gas reaches the cooler tube walls before the reaction is completed, the alkali metals will tend to condense on the cooler metal. In this case, further sulfate formation can occur on the metal under the release of HCl, and that causes high chlorine partial pressures and enhanced corrosion.

Without $SO_2$ at 500° C., NaCl and iron oxides can form $Cl_2$:

$$2NaCl+Fe_2O_3+\tfrac{1}{2}O_2=Na_2Fe_2O_4+Cl_2. \qquad [3]$$

$$6NaCl+2Fe_3O_4+2O_2=3Na_2Fe_2O_4+3Cl_2 \qquad [4]$$

Calculations of the dissociation constant of HCl as a function of temperature indicate that chlorine is present as $Cl_2$ under oxidizing conditions up to gas temperatures of 600° C., whereas above 600° C. formation of HCl is enhanced in the presence of water vapor according to the reaction:

$$H_2O+Cl_2=2HCl+\tfrac{1}{2}O_2 \qquad [5]$$

Rademakers, et al., state that at about 500° C., $Cl_2$ can penetrate pores or cracks in an oxide layer. At the low oxygen partial pressures that exist near the metal-oxide scale boundary, the metal chlorides are the more stable phase. Reactions 3 and 4 can result in a $Cl_2$ partial pressure sufficiently high that it reacts directly with the steel to form $FeCl_2$:

$$Fe+Cl_2=FeCl_2 \text{ (solid)} \qquad [6]$$

The vapor pressures of metal chlorides will depend primarily on the temperature and the HCl content of the gas. In addition, the type of oxide (and alloy) can considerably influence the vapor pressure. The vapor pressure of $FeCl_2$ is already relatively high at low temperatures. As a result, formation of $FeCl_2$ can decrease the adherence of the oxide scale or can cause spallation of the oxide layer.

Rademakers, et al., explain that iron chlorides form and migrate out from the corrosion product due to their volatility. At higher oxygen partial pressures near the oxide-gas interface, these chlorides are then converted to oxides and liberate chlorine. These new oxides are not formed as a perfect layer and do not offer protection. Part of the liberated chlorine migrates back through the oxide/deposit to react with the metal at the oxide-metal interface, and form metal chlorides again:

$$FeCl_2 \text{ (solid)} = FeCl_2 \text{ (gas)} \quad [7]$$

$$4FeCl_2 + 3O_2 = Fe_2O_3 + 2Cl_2 \quad [8]$$

$$3FeCl_2 + 2O_2 = Fe_3O_4 + 3Cl_2 \quad [9]$$

In this process, the chlorine has a catalytic effect on the oxidation of the metal resulting in enhanced corrosion.

The kinetics of active oxidation is mainly determined by the evaporation and outward diffusion of $FeCl_2$. Similar chlorine corrosion and regeneration cycles may proceed via $FeCl_3$ and it is possible for the ferrous iron to be oxidized to the ferric state, which liberates chlorine when oxidized.

$$4FeCl_2 + 4HCl + O_2 = 4FeCl_3 + 2H_2O \quad [10]$$

$$4FeCl_3 + 3O_2 = 2Fe_2O_3 + 4Cl_2 \quad [11]$$

The volatility of different compounds can be compared based on the temperature T4 (temperature at which the vapor pressure reaches $10^{-4}$ bar), and vapor pressure values for some compounds are given in Table 1.

TABLE 1

| T4 Temperatures of Metal Chlorides of Main Alloying Elements | |
|---|---|
| Metal chloride | T4 (° C.) |
| $FeCl_2$ | 536 |
| $FeCl_3$ | 167 |
| $CrCl_2$ | 741 |
| $CrCl_3$ | 611 |
| $NiCl_2$ | 607 |

From the above, Rademakers, et al., conclude that low alloy steels and iron-base alloys have limited resistance against active oxidation. High alloyed materials, nickel base alloys in particular, have a much better resistance, which may be because chlorides are more difficult to form and, once formed, have a relatively low volatility. Except for the $FeCl_3$, most T4 temperatures are well above 500° C. indicating that this mechanism is most relevant to superheaters and less to evaporators.

Corrosion of heat transfer surfaces in boilers has been a major problem, particularly WTE units which generate highly corrosive flue gases, and continues to trouble the industry. It would be desirable to have a technology that could mitigate corrosion and slag at the same time.

There remains a present challenge to provide a process for taking necessary corrective action to address the slag in boilers, particularly in WTE units, to reduce or eliminate down time for cleaning while also treating the corrosion before damage becomes excessive and requires expensive repair and shut down.

SUMMARY OF THE INVENTION

It is an object of the invention to provide a method for reducing the severity of slagging while simultaneously controlling corrosion of the high temperature surfaces of a boiler, particularly a waste to energy boiler under operating load.

It is another object of the invention to provide a method for reducing the severity of slagging and corrosion of the high temperature surfaces of a boiler, particularly a waste to energy boiler by the introduction of inexpensive chemical treatment agents that can modify the corrosion process and change the physical nature of the deposited.

It is another object of the invention to provide a method for simultaneously reducing slagging and corrosion of the high temperature surfaces of a boiler by introducing chemicals by targeted injection, which chemicals reduce slag deposition, make any deposited slag more friable and also lessen the problem of corrosion.

It is yet another object of the invention to provide a method for simultaneously reducing slagging and corrosion of the high temperature surfaces of a boiler by introducing chemicals by targeted injection, which chemicals produce a friable slag which can be easily removed, preferably without shutting the boiler down.

It is yet another object of the invention to provide a method for simultaneously reducing slagging and corrosion of the high temperature surfaces of a boiler by selectively targeting injection of corrosion reducing and slag reducing chemicals whereby corrosion is reduced, lower quantities of slag are deposited and the slag deposits are more easily removed than achieved with the prior art.

It is yet another object of the invention to provide a method for simultaneously reducing slagging and corrosion of the high temperature surfaces of a boiler whereby the slag that does form can be removed without excessive tube erosion.

These and other objects of the invention are achieved by the invention, which provides a method for corrosion control in a boiler, particularly a waste to energy boiler, wherein the process involves the targeted introduction of corrosion and slag treatment chemicals.

In one aspect the invention will comprise: identifying the location of at least one slagging problem area in a boiler; introducing a slag control chemical comprising magnesium oxide or hydroxide into combustion gases in a location identified as having a slagging problem; identifying the location of at least one corrosion problem area in a boiler; and introducing a corrosion control chemical comprising a sulfate salt, bisulfite salt, sulfuric acid, or sulfur into combustion gases in a location identified as having a corrosion problem.

Figure 2:
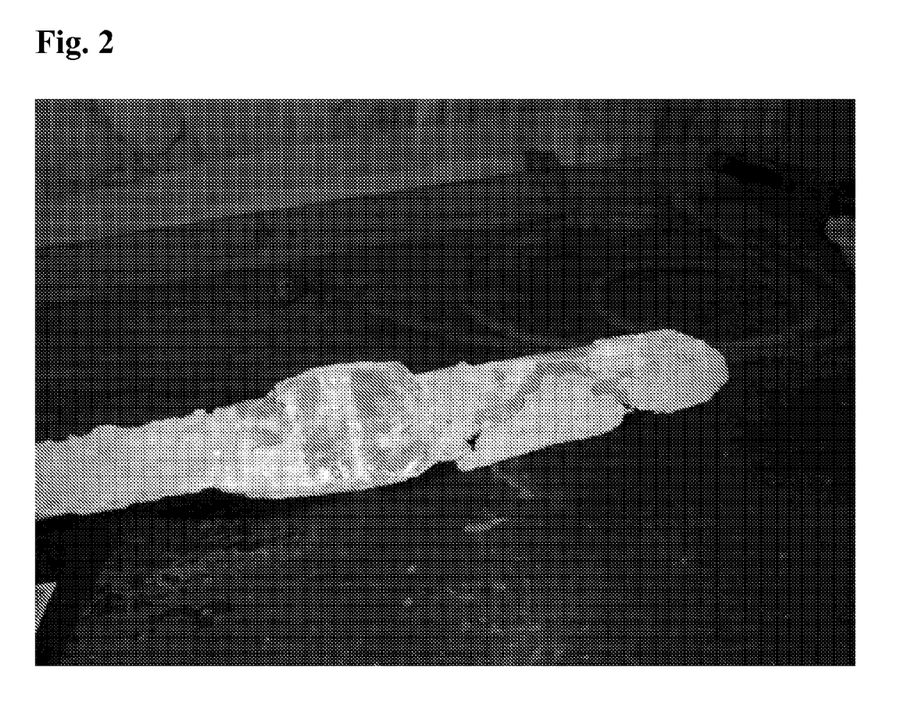
FIG. 2 is a photograph showing a superheater test probe covered with friable deposits of slag.

Performance of the process as described above and further described below with reference to preferred aspects, has been found to effectively reduce corrosion of super heater tube pendants in WTE boilers and to result in less slag being deposited than with conventional treatments. In operation, these slag deposits will be sufficiently friable to be removed by relatively moderate application of physical energy, thus saving time and reducing any damage to the tubes by the cleaning process. The slag deposits are less voluminous and less in weight and are removed quickly. The use of water, steam or air jets of conventional design as in soot blowers or as may otherwise be configured to be effective and other means including mechanical contact devices, including those that utilize laser means. It is an advantage of the invention that slag can be removed with little or no shut down of a boiler. FIG. 2 is a photograph showing a test probe covered with friable deposits of slag.

BRIEF DESCRIPTION OF THE DRAWINGS

The invention will be better understood and its advantages will become more apparent from the following detailed description, especially when taken with the accompanying drawings, wherein.

DETAILED DESCRIPTION OF THE INVENTION

Figure 3:
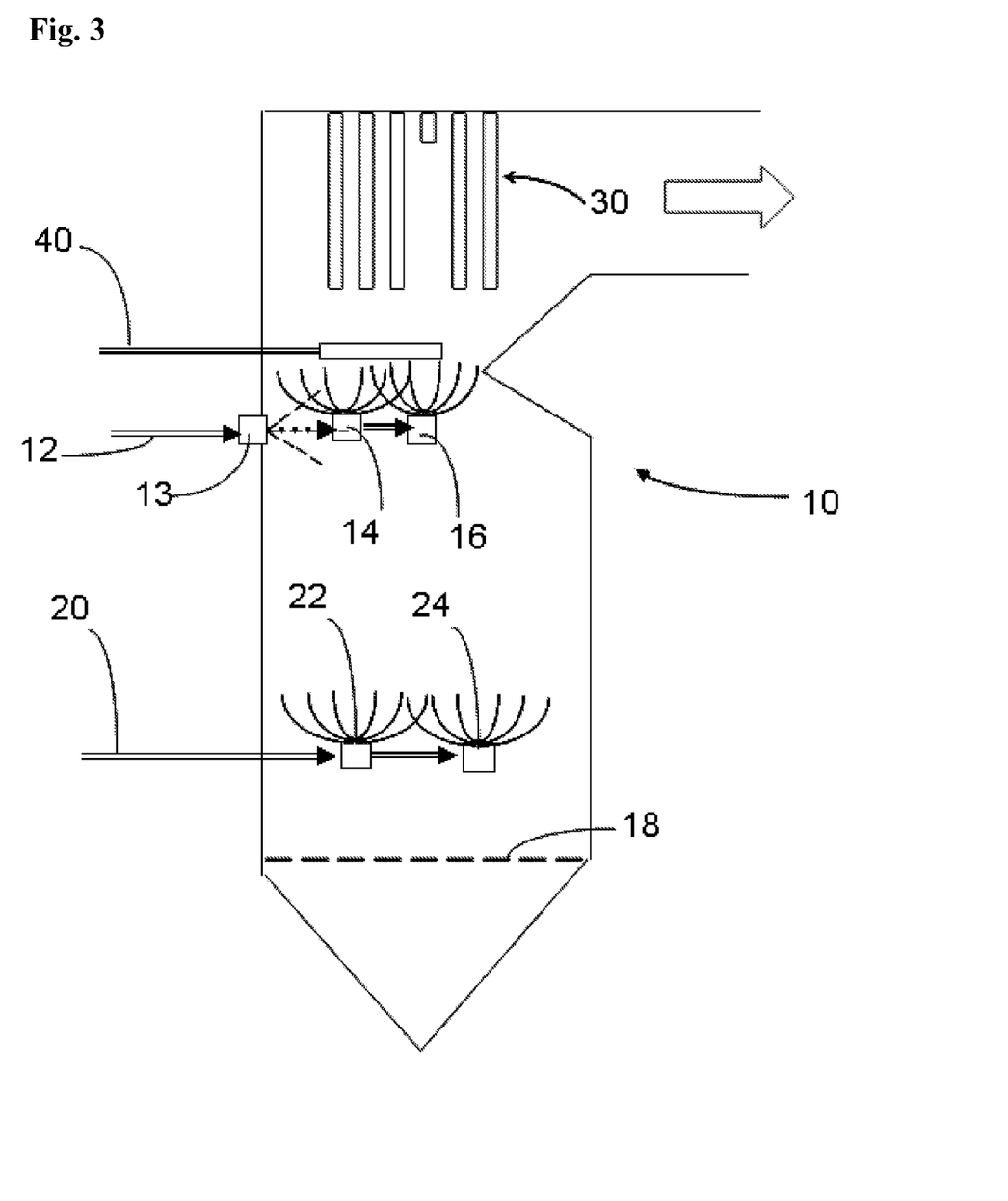
FIG. 3 is a schematic representation of a typical WTE boiler with points of injection of active treatment chemicals.

The invention provides processes for corrosion control in a boiler, particularly a waste to energy (WTE) boiler, wherein the process involves the targeted introduction of corrosion and slag treatment chemicals. The schematic of FIG. 3 shows a WTE boiler 10 as configured by the present invention. Points of injection of active slag treatment chemicals are shown generally from line 12 and six injectors (two on the front and two on each side). Here, injectors 13 on the front and 14 and 16 on the facing side can be seen. Injection is based on a first process step of identifying the location of at least one slagging problem area in a boiler. A slag control chemical comprising magnesium oxide or hydroxide will be introduced into combustion gases at these locations. Points of injection of active corrosion control chemicals, preferably just above grate 18 in a WTE boiler, are shown from line 20, though injectors shown at 22 and 24, with like injectors preferably on the opposite side. This injection can also based on a first process step of identifying the location of at least one corrosion problem area in a boiler. A corrosion control chemical comprising a sulfate salt, bisulfite salt, sulfuric acid, or sulfur is introduced into the combustion gases at these locations or others as will be determined. Injection of all chemicals is preferably accomplished prior to the super heater tubes, if any, represented as 30. If desired a probe 40 can be employed as will be described to monitor corrosion.

Performance of the process will be described below with reference to preferred aspects, which have been found to effectively reduce corrosion of super heater tube pendants in WTE boilers and to result in less slag being deposited than with conventional treatments. It is, however, within the scope of the invention to utilize the process on other types of combustors experiencing the same types of problems, i.e., slagging and corrosion. For all large scale boilers and combustors, these slag deposits will be made more friable, capable of being removed by relatively moderate application of physical energy. The slag deposits will be less voluminous and less in weight and are removed quickly. The use of water, steam or air jets of conventional design as in soot blowers or as may otherwise be configured to be effective and other means including mechanical contact devices, including those that utilize laser means. It is an advantage of the invention that slag can be removed with little or no shut down of a boiler. FIG. 2 is a photograph showing a superheater test probe covered with friable deposits of slag. As can be seen in this paragraph, the slag is so light and nonadherant that it falls from the test section of tube when removed from the boiler and placed on a surface for examination. The slag deposits when the present invention is used will desirably be less solid (i.e., more porous) and less strong to compressive stress than slag from untreated operation. In preferred cases, they will easily crush when compressed with modest pressure, e.g., by hand. By way of example, some untreated slag deposits can have compressive yield points of in excess of about 1000 psi; but when the present invention is employed, the yield stress will be less than this, preferably being less than about 100 psi, more preferably less than about 10 psi, and desirably less than about 1 psi. Friable deposits can be more easily removed.

The problems of slagging and corrosion have been connected to some extent in the context of boiler operation. However, the invention for the first time presents a process for treating both selectively and simultaneously with the surprising result that less slag is formed while corrosion is reduced, and the slag that does form is more friable and less dense.

The invention controls normally difficult slagging deposits by determining the location of slagging problems and adding treatment chemicals to the fuel and/or into the furnace at locations and in quantities sufficient to treat the ash produced. This technology provides for targeted chemical introduction where the chemical is directed at trouble spots in a boiler. Typical slag control chemicals include magnesium oxide and magnesium hydroxide. See, in this regard, U.S. Pat. Nos. 5,740,745 and 5,894,806 and U.S. Patent Publication No. 20050150441 and the references cited therein. These chemicals, especially in the process of the invention, reduce the severity of slagging and make cleaning significantly easier. The invention reduces the severity of slagging making it possible for the reduced application of mechanical energy to effectively clean heat exchange surfaces with little or no boiler shut down.

The process of the invention identifies the location of at least one slagging problem area in a boiler, say at the super heater tubes 22, in FIG. 3, and then introducing a slag control chemical comprising magnesium oxide or hydroxide into combustion gases in a location identified as having a slagging problem, such as through injectors 12 in FIG. 3. Targeted injection of the in-furnace injection chemical will require locating introduction points on the furnace wall where introduction of targeted in-furnace treatment chemical could be accomplished. And, based on the determinations of this procedure, targeted in-furnace treatment chemical is introduced, such as in the form of a spray. The droplets are desirably in an effective range of sizes traveling at suitable velocities and directions to be effective as can be determined by those skilled in the art. These drops interact with the flue gas and evaporate at a rate dependent on their size and trajectory and the temperatures along the trajectory. Proper spray patterns result in highly efficient chemical distributions.

As described in the above-identified patents, a frequently used spray model is the PSI-Cell model for droplet evaporation and motion, which is convenient for iterative CFD solutions of steady state processes. The PSI-Cell method uses the gas properties from the fluid dynamics calculations to predict droplet trajectories and evaporation rates from mass, momentum, and energy balances. The momentum, heat, and mass changes of the droplets are then included as source terms for the next iteration of the fluid dynamics calculations, hence after enough iterations both the fluid properties and the droplet trajectories converge to a steady solution. Sprays are treated as a series of individual droplets having different initial velocities and droplet sizes emanating from a central point.

Correlations between droplet trajectory angle and the size or mass flow distribution are included, and the droplet frequency is determined from the droplet size and mass flow rate at each angle. For the purposes of this invention, the model should further predict multi component droplet behavior. The equations for the force, mass, and energy balances are supplemented with flash calculations, providing the instantaneous velocity, droplet size, temperature, and chemical composition over the lifetime of the droplet. The momentum, mass, and energy contributions of atomizing fluid are also included. The correlations for droplet size, spray angle, mass flow droplet size distributions, and droplet velocities are found from laboratory measurements using laser light scattering and the Doppler techniques. Characteristics for many types of nozzles under various operating conditions have been determined and are used to prescribe parameters for the CFD model calculations. When operated optimally, chemical efficiency is increased and the chances for impingement of droplets directly onto heat exchange and other equipment surfaces is greatly reduced. Average droplet sizes within the range of from 20 to 1000 microns are typical, and most typically fall within the range of from about 100 to 600 microns.

One preferred arrangement of injectors for introducing active chemicals for reducing slag in accordance with the invention employ multiple levels of injection to best optimize the spray pattern and assure targeting the chemical to the point that it is needed. However, the invention can be carried out with a single zone, e.g., in the upper furnace, where conditions permit or physical limitations dictate. Typically, however, it is preferred to employ multiple stages, or use an additive in the fuel and the same or different one in the upper furnace. This permits both the injection of different compositions simultaneously or the introduction of compositions at different locations or with different injectors to follow the temperature variations which follow changes in load.

As discussed above, the problem of high temperature corrosion within waste to energy boilers by chlorides is one of the most costly in the industry. The chemistry of the corrosion is explained above with reference to FIG. 1, which is a schematic that outlines a probable sequence of chemical reactions to help explain the occurrence and progression of corrosion of incinerator boiler tubes. Where chloride has been identified as a cause of the problem, the corrosion can be controlled by introducing $SO_3$ or a precursor of it into the corrosive atmosphere in a manner as to most directly attack the problem. In this regard, the teachings of Smyrniotis, et al., U.S. Pat. Nos. 5,740,745 and 5,894,806 and U.S. patent application Ser. No. 10/754,072, are instructive of the processing arrangements and control that may be utilized and enhanced with the invention.

The monitoring of corrosion and the correction of it by the introduction of $SO_3$ or precursor chemicals in a targeted fashion can be effective in reducing corrosion and its adverse consequences. The invention provides for the addition of a sulfur compound capable of releasing $SO_2$ or $SO_3$, preferably in the form of a sulfate salt, bisulfite salt, sulfur or sulfuric acid, e.g., $H_2SO_4$, in concentrations and at locations which will interfere with the chloride chemistry as outlined above and help maintain the chloride in gaseous form. An alternative source of $SO_2$ or $SO_3$ is Sulfur burner technology. To the extent that the materials are corrosive, care should be taken in equipment selection, and diaphragm pumps or the like may be most appropriate. The invention thus can enhance the use of the process and chemicals by carefully applying limited amounts of chemical in a control regimen that will save much greater amounts than would otherwise be spent in superheater tube replacements, materials upgrades and system down time.

Corrosion is desirably monitored, such as by a device and technique as described in copending U.S. patent application Ser. No. 11/383,648, filed May 16, 2006. Another type of corrosion monitor measures electrochemical noise occurring at the surface of the tubes while that surface is exposed to combustion products. U.S. Pat. No. 6,478,948 to Breen, et al., describes such a corrosion monitor. The details of these corrosion monitors are incorporated herein by reference. A corrosion monitor having an associated computer and software determines a corrosion rate from the measured values. That rate is compared to a standard to determine if the rate is within acceptable limits. If not, the rate and/or location of chemical addition can be changed. The probe 40, as the probe of Breen, et al., or as described in U.S. patent application Ser. No. 11/383,646, can be jacketed to control its temperature, preferably to be of constant temperature.

According to the invention, sulfur bearing materials in a water based mixture can be introduced generally or are targeted for injection to the trouble spots in the boiler and as close to the flame as practical in a form designed to maximize the conversion of the chloride salts to their sulfate forms. The primary chemical reaction is believed to be:

2XCl+SO$_3$+H$_2$O+→X2SO4+2HCl

Where X can be a suitable metal anion, e.g., an alkali metal such as sodium, potassium or the like.

It is believed that without $SO_3$ at 500° C., NaCl and iron oxides present in deposits can form $Cl_2$ as discussed above. It is believed important to reduce the presence of $Cl_2$ near the metal tubes at temperatures above about 500° C., and the introduction of an $SO_3$ reagent is a preferred manner of corrosion control according to the invention. The preferred $SO_3$ reagent for application to deposits as they form is a sulfate salt (e.g., $ZnSO_4$) a bisulfite salt, e.g., sodium bisulfite, sulfur and/or sulfuric acid, or in-situ or on-line generated $SO_3$ from a combustion of sulfur, at any concentration suitable for use. It is possible to use concentrated solutions of sodium bisulfite, $ZnSO_4$ and/or sulfuric acid, but the reagent is generally diluted with sufficient water to permit application to the desired area in the boiler. Typically, concentrations of from about 10 to 90 weight percent will be employed at a molar ratio sulfur to chlorine in the combustion gases of from 1:3 to 3:1. Ratios near stoichiometric based on chlorine are preferred.

Before and following selection of corrosion control chemicals and the locations for targeted in furnace injection, injection regimen and chemical selection and introduction parameters are monitored with the aid of the method and apparatus of the invention to adjust one or more control parameters to reduce corrosion. The processing and chemicals can be of the type described in U.S. Pat. Nos. 5,740,745 and 5,894,806 and U.S. patent application Ser. No. 10/754,072, all to Smyrniotis, et al., which are incorporated herein by reference, to reduce the problems with chloride corrosion in waste to energy boilers.

The following example is provided to further illustrate and explain the invention, without being limiting in any regard. Unless otherwise indicated, all parts and percentages are based on the weight of the composition at the particular point of reference.

EXAMPLE 1

In a baseline run, magnesium hydroxide [Mg(OH)$_2$] was fed on one level at 1 pound per ton of fuel (RDF) at a WTE plant.

In a series of test runs, sulfuric acid (93% by weight) and sodium bisulfite (SBS) were fed at another level at 4.4 lbs (42%, by weight, solution in water) per ton of RDF fuel while also feeding the magnesium hydroxide as in the baseline run. One sulfuric acid and two SBS runs were made.

The data permits the following observations:
1. The corrosion rate reduction was 60% which is very similar to the first SBS run (61%) and the H$_2$SO$_4$ run. (60%) This is a good correlation.
2. Both SBS runs created a slag that was so friable that it literally crumbles when touched.
3. After the first SBS run, the WTE boiler operator performed a scheduled outage and inspection. It was noted that the clean up time was fast and the deposits from slag were very friable.

4. During the second SBS run (repeatability phase) a piece of slag fell and an unscheduled emergency shut down was initiated. The WTE boiler operator called in additional workers to help break the slag into smaller pieces to allow the slag to fall through the grate; however, while this was expected to take well over an hour, the deposits were broke apart in only a few minutes.

5. Samples of the slag from the baseline run and the two SBS runs where obtained and show the following analysis:

| Sample Appearance: Slightly Magnetic Red-Brown Pieces Boiler (Fireside) Deposit Analysis — Baseline Elemental Analysis by X-Ray Fluorecence | |
|---|---|
| The sample prepartion was: Ashed at 925° C. | |
| Iron as (Fe2O3) | 51% |
| Sulfur as (SO3) | 13% |
| Calcium as (CaO) | 8% |
| Sodium as (Na2O) | 6% |
| Silicon as (SiO2) | 5% |
| Aluminum as (Al2O3) | 2% |
| Potassium as(K2O) | 2% |
| Chloride as (Cl) | 1% |
| Magnesium as (MgO) | 1% |
| Zinc as (ZnO) | 1% |
| Total From XRF: | 90 % |
| The results for the XRF analysis were normalized to Loss at 925° C. Thus. XRF + L925 = 100% Elemental Fluorine to Uranium were measured. The following common element were not datacard or were below the reporting limit of < 0.5% | |

| Ba | Co | Cr | Cu | F | Mn | Mo | Ni | P | Pb | Sn | Sr | Ti | V |
|---|---|---|---|---|---|---|---|---|---|---|---|---|---|

| | |
|---|---|
| CHL | |
| CH2CL2 Extractables | <1% |
| CO2 | |
| Carbonate (CO2) | <1% |
| L925 | |
| Loss at 925° C. | 9% |
| Ash at 925° C. | 91% |
| PHIS | |
| pH of a 1% Slurry | 8.2 |
| Additional Data | |
| Unbaroed Carbon ( C ) | <1% |
| Nitrogen ( N ) | <1% |
| Carbonate ( CO2 ) | <1% |
| Volatile Sulfur ( SO3) | <1% |
| Balance ( H2O ) | 9% |
| (The sum of there components should approximate the Loss at 925° C.) | |

| Sample Appearance: Slightly Magnetic Tan Pieces Boiler (Fireside) Deposit Analysis — Baseline Elemental Analysis by X-Ray Fluorecence | |
|---|---|
| The sample prepartion was: Ashed at 925° C. | |
| Sulfur as (SO3) | 23% |
| Iron as (Fe2O3) | 19 % |
| Calcium as (CaO) | 14% |
| Sodium as (Na2O) | 10% |
| Chloride as (Cl) | 6% |
| Silicon as (SiO2) | 6% |
| Potassium as (K2O) | 4% |
| Aluminum as (Al2O3) | 3% |
| Magnesium as (MgO) | 1% |
| Phosphorus as (P2O5) | 1% |
| Titanium as (TuO2) | 1% |
| Zinc as (ZnO) | 1% |
| Total From XRF: | 89 % |

-continued

The results for the XRF analysis were
normalized to Loss at 925° C.
Thus. XRF + L925 = 100%
Elemental Analysis to Uranium were measured.
The following common element were not detected or
were below the reporting limit of < 0.5%

| Ba | Co | Cr | Cu | F | Mn | Mo | Ni | P | Pb | Sn | Sr | V |
|---|---|---|---|---|---|---|---|---|---|---|---|---|

CHL
   CH2CL2 Extractables . . . . . . . . . . . . . . . . . . . . . . . . . . . <1%
CO2
   Carbonate (CO2) . . . . . . . . . . . . . . . . . . . . . . . . . . . <1%
L925
   Loss at 925° C. . . . . . . . . . . . . . . . . . . . . . . . . . . . . 11%
   Ash at 925° C. . . . . . . . . . . . . . . . . . . . . . . . . . . . . 89%
PH1S
   pH of a 1% Slurry . . . . . . . . . . . . . . . . . . . . . . . . . . . 8.5
Additional Data Unbaroed Carbon ( C ) . . . . . . . . . . . . . . . . . . . . . . . . . . . <1%
Nitrogen ( N ) . . . . . . . . . . . . . . . . . . . . . . . . . . . <1%
Carbonate ( CO2 ) . . . . . . . . . . . . . . . . . . . . . . . . . . . <1%
Volatile Sulfur ( SO3 ) . . . . . . . . . . . . . . . . . . . . . . . . . . . <1%
Balance ( H2O ) . . . . . . . . . . . . . . . . . . . . . . . . . . . 11%

(The sum of there components
should approximate the less at 925° C.)

---

Sample Appearance: Sliguly Maguetic Brown Pieces
Boiler (Fireside) Deposit Analysis — SBS, Run 2
Elemental Analysis by X-Ray Fluorescence The sample preparartion was: Ashed at 925° C.

Sulfur as (SO3) . . . . . . . . . . . . . . . . . . . . . . . . . . . 23%
Iron as (Fe2O3) . . . . . . . . . . . . . . . . . . . . . . . . . . . 20%
Calcium as (CaO) . . . . . . . . . . . . . . . . . . . . . . . . . . . 15%
Silicon as (SiO2) . . . . . . . . . . . . . . . . . . . . . . . . . . . 12%
Sodium as (Na2O) . . . . . . . . . . . . . . . . . . . . . . . . . . . 10%
Aluminum as (Al2O3) . . . . . . . . . . . . . . . . . . . . . . . . . . . 4%
Potassium as (K2O) . . . . . . . . . . . . . . . . . . . . . . . . . . . 3%
Chloride as (Cl) . . . . . . . . . . . . . . . . . . . . . . . . . . . 2%
Magnesium as (MgO) . . . . . . . . . . . . . . . . . . . . . . . . . . . 1%
Phosphorus as (P2O5) . . . . . . . . . . . . . . . . . . . . . . . . . . . 1%
Titanium as (TiO2) . . . . . . . . . . . . . . . . . . . . . . . . . . . 1%
Zinc as (ZnO) . . . . . . . . . . . . . . . . . . . . . . . . . . . 1%
Total From IMF: 93 %

The results for the XRF analysis were
normalized to Loss at 925° C.
Thus. XRF + L925 = 100%
Elements Fluorine to Uranium were measured.
The following common element were not detected or
were below the reporting limit of < 0.5%

| Ba | Co | Cr | Cu | F | Mn | Mu | Ni | Pb | Sn | Sr | V |
|---|---|---|---|---|---|---|---|---|---|---|---|

CHL
   CH2CL2 Extractables . . . . . . . . . . . . . . . . . . . . . . . . . . . <1%
CO2
   Carbonate (CO2) . . . . . . . . . . . . . . . . . . . . . . . . . . . <1%
L925
   Loss at 925 C . . . . . . . . . . . . . . . . . . . . . . . . . . . 6%
   Ash at 925° C . . . . . . . . . . . . . . . . . . . . . . . . . . . 94%
PH1S
   pH of a 1% Slurry . . . . . . . . . . . . . . . . . . . . . . . . . . . 9.1
Additional Data Unbaroed Carbon ( C ) . . . . . . . . . . . . . . . . . . . . . . . . . . . <1%
Nitrogen ( N ) . . . . . . . . . . . . . . . . . . . . . . . . . . . <1%
Carbonate ( CO2 ) . . . . . . . . . . . . . . . . . . . . . . . . . . . <1%
Volatile Sulfur ( SO3 ) . . . . . . . . . . . . . . . . . . . . . . . . . . . <1%
Balance ( H2O ) . . . . . . . . . . . . . . . . . . . . . . . . . . . 6%

(The sum of there components
should approximate the less at 925° C.)

From the above data, we can draw the following conclusions:
- a. The baseline sample indicates 51% iron (Fe) content. The treated samples indicate 19-20% Fe. That is roughly a 61% decrease in Fe.
- b. Qualitative analysis (X-ray diffraction) indicates that the treated slag did not have iron oxide in the form of magnetite ($Fe_3O_4$).
- c. The treated slag samples indicate additional sulfation has taken place. In particular the sulfates are combining with calcium (Ca), potassium (K) and sodium (Na).
- d. The sulfation of Ca, Na and K in the samples is significant for a couple of reasons. Ca, Na and K have an affinity for chlorine (Cl). In short, they form salts which are corrosive. Sulfating Ca, Na and K inhibits the salts from forming. It should be noted that the chemistry of the slag is changing such that the eutectic is also changing. The relatively low melting points of Na and K, for example, can result in slag that is more tenacious. We believe that this plays a role in making the slag more friable.
- e. The observation of decreased Fe in the test samples versus the baseline is significant. There are less iron oxides because the corrosion process has slowed down. In short, there is less iron because there is less corrosion. Less iron results in more friable slag not only from a eutectic standpoint, but also from a structural standpoint.
- f. In short the chemistry and resulting mechanical properties of the slag has changed such that the crush strength is affected.

EXAMPLE 2

In a baseline run, magnesium hydroxide [$Mg(OH)_2$] was fed on one level at 1 pound per ton of fuel (RDF) at a WTE plant. In a test run, sodium bisulfite (SBS) was fed at another level at 4.4 pounds (42%, by weight, solution in water) per ton of RDF fuel while also feeding the magnesium hydroxide as in the baseline run.

It was observed that slag deposits removed from a test probe in the boiler were extremely friable.

The above description is for the purpose of teaching the person of ordinary skill in the art how to practice the invention. It is not intended to detail all of those obvious modifications and variations, which will become apparent to the skilled worker upon reading the description. It is intended, however, that all such obvious modifications and variations be included within the scope of the invention which is defined by the following claims. The claims are meant to cover the claimed components and steps in any sequence which is effective to meet the objectives there intended, unless the context specifically indicates the contrary.

The invention claimed is:

1. A process for controlling slag and corrosion in a boiler, reducing both and making the slag less dense and more friable, comprising: identifying the location of at least one slagging problem area in a boiler; introducing a slag control chemical comprising magnesium oxide or hydroxide into combustion gases in a location identified as having a slagging problem; identifying the location of at least one corrosion problem area in a boiler; and introducing a corrosion control chemical comprising a sulfate salt, bisulfite salt, sulfuric acid, or sulfur into combustion gases in a location identified as having a corrosion problem.

2. A process according to claim 1, wherein: a constant temperature probe having a corrodible surface is positioned in a known position in a boiler; the probe is periodically removing for visual and/or physical observation; based on the observations of the probe and comparison with data for boiler components such as tubes, the degree of corrosion on the probe is calibrated with what could be expected of the boiler components; and then the observations of the probe as calibrated are utilized to control introduction of corrosion control chemicals into the boiler.

3. A process according to claim 1, wherein: the degree of corrosion in a boiler is monitored utilizing a probe and signal processor for observing electrochemical noise in a probe within the furnace and comparing that information to known values to provide a signal that corresponds to corrosion rate.

4. A process according to claim 3, wherein: the probe is a constant temperature probe.

5. A process according to claim 1 wherein the boiler is a waste to energy boiler.

6. A process according to claim 1 wherein the compressive yield strength of slag forming in the boiler is less than about 1000 psi.

7. A process according to claim 6 wherein the compressive yield strength of slag forming in the boiler is less than about 100 psi.

8. A process according to claim 1, wherein: probes for a corrosion monitor are placed in original positions and the original introduction parameters for the introduction of corrosion control chemicals are based on computational fluid dynamic determinations.

9. A process according to claim 1, wherein: a chemical composition comprising an $SO_2$ or $SO_3$ or precursor of either is introduced into the corrosive atmosphere in a manner effective to maintain chlorine gas in gaseous form and the sulfate salts of the metal being corroded in solid form.

10. A process according to claim 9, wherein: the chemical composition comprising $SO_2$ or $SO_3$ or precursor of either comprises a sulfate salt, bisulfite salt, sulfuric acid, or sulfur in amounts sufficient to reduce corrosion.

11. A process according to claim 1, wherein: corrosion is monitored by use of a probe capable of fixing to a boiler exterior and extending into a boiler to an extent necessary to reach a suspected trouble point for corrosion; a source of cooling fluid and means for directing the fluid into the probe for cooling the probe; and temperature sensing means associated with the probe and control means for controlling supply of the fluid to the probe; wherein the probe is adapted to permit insertion and withdrawal from the boiler for visual and physical observation.

* * * * *